United States Patent [19]
Khalkhali et al.

[11] Patent Number: 5,803,913
[45] Date of Patent: *Sep. 8, 1998

[54] NUCLEAR MEDICINE STEREOTAXIC LOCALIZATION APPARATUS FOR BREAST CARCINOMAS AND METHOD

[76] Inventors: Iraj Khalkhali, 6412 Corsini Pl., Rancho Palos Verdes, Calif. 90732; Ismael Mena, Elcanal 8122, Santiago, Chile; Linda Diggles, 21210 Hobart Blvd., Torrance, Calif. 90501; Douglas M. Diggles, Sr., 754 S. Alpine Way, Bodfish, Calif. 93205; Robert E. Diggles, 21210 Hobart Blvd., Torrance, Calif. 90501

[*] Notice: The term of this patent shall not extend beyond the expiration date of Pat. No. 5,595,177.

[21] Appl. No.: 597,139

[22] Filed: Feb. 6, 1996

Related U.S. Application Data

[63] Continuation-in-part of Ser. No. 253,419, Jun. 3, 1994, Pat. No. 5,595,177.

[51] Int. Cl.$^6$ .................................................. A61B 5/05
[52] U.S. Cl. ................................................ 600/407; 600/431
[58] Field of Search ........................... 128/653.1, 654; 378/37, 162–164, 68, 193, 195, 205, 206, 208; 5/601; 606/130; 600/407, 431

[56] References Cited

U.S. PATENT DOCUMENTS

| | | | |
|---|---|---|---|
| 3,556,081 | 1/1971 | Jones | 378/37 |
| 4,875,478 | 10/1989 | Chen | 606/130 |
| 4,890,311 | 12/1989 | Saffer | 378/163 |
| 5,078,142 | 1/1992 | Siczek et al. | 378/37 |
| 5,289,520 | 2/1994 | Pellegrino et al. | 378/208 |
| 5,386,447 | 1/1995 | Siczek | 378/37 |
| 5,437,280 | 8/1995 | Hussman | 606/130 |

Primary Examiner—Brian L. Casler
Attorney, Agent, or Firm—Fulwider Patton Lee & Utecht, LLP

[57] ABSTRACT

A nuclear medicine guided system and method for stereotaxic localization of breast carcinoma lesion sites, used in conjunction with a nuclear medicine detection device, of a patient who has been injected with a radioactive substance which preferentially accumulates in carcinoma lesion sites. The system includes a table, a pair of fenestrated paddles, and a guide means. The table has a top surface, upon which the patient lies in a prone position, and at least one opening through which the patient's breast being examined will pendulously protrude therethrough. A pair of fenestrated paddles are positioned under the bottom surface of the table in the vicinity of the opening, and are moveable relative to each other to compress the patient's breast therebetween. The guide is positioned under the table in the vicinity of the opening. The guide has plurality of moveable sighting guides, each moveable along one of three orthogonal axes, and each sighting guide having a radioactive sighting line located thereon. The moveable sighting guides are moved to line up with the lesion site, as detected by the nuclear medicine detector device, to localize the carcinoma lesion sites in three dimensions and in real-time.

22 Claims, 5 Drawing Sheets

NUCLEAR MEDICINE STEREOTAXIC LOCALIZATION APPARATUS FOR BREAST CARCINOMAS AND METHOD

CROSS REFERENCE TO RELATED APPLICATIONS

This is a continuation-in-part to U.S. application Ser. No. 08/253,419, filed Jun. 3, 1994, now U.S. Pat. No. 5,595,177, to Mena et al., entitled "SCINTIGRAPHY GUIDED STEREOTAXIC LOCALIZATION APPARATUS FOR BREAST CARCINOMAS."

BACKGROUND OF THE INVENTION

1. Field of the Art

This invention relates to the field of breast lesion localization and biopsy, and more particularly to an apparatus and method for localizing a breast carcinoma lesion site by nuclear medicine in three dimensions and in real-time.

2. Description of the Prior Art

The occurrence of breast cancer is a leading cause of death for women. Women are advised to conduct breast self examination for palapable lumps or bumps on a monthly basis, and after the age of 40, to undergo mammography at least on a bi-annual basis in order to detect nonpalapable lesions. Presently, special roentgenography, or x-ray techniques for photographically studying the mammary gland, or breast, are utilized to locate lesion with greater success than with self-examination, particularly with small lesion located deep in the breast. However, one major problem with traditional x-ray mammography is that there is little selectivity in what is imaged. In addition to malignant carcinoma tumors, generally harmless calcifications, proliferative changes, fibroadenomas, and fibrocystic changes show up. Indeed, while x-ray mammography has a high sensitivity of 85–90%, it currently predicts malignancy in only about 20–30% of mammography suspicious lesions. Since the radiologist has great difficulty in distinguishing malignancy from harmless lesions, biopsy and tissue sampling must be carried out to determine if the lesion is malignant. In fact, in around 80% of the cases where biopsies are performed, the lesions prove not to be malignant.

In order to effectively conduct the x-ray mammography, the patient's breast being imaged must be compressed with great and uncomfortable force to squeeze the breast to a thickness of about three to four and a half centimeters so that the x-rays can adequately penetrate the breast and develop the film lying behind the breast. This process must be conducted in two separate planes. First, the breast is compressed in a horizontal plane, so a cranial and caudal projection can be taken. The next projection taken is a mediolateral oblique view, wherein the breast is compressed in a vertical plane. These two initial views taken together make up the screening mammography.

The radiologist will then read the x-ray negatives to determine if there are any lesions or other signs of lesions in the breast. If the radiologist sees any suspicious lesions, then "special views" are taken. Actually, the same views as in a screening are carried out, except that the compressed breast is slightly displaced from the film plate to effect magnification of any lesions in the breast. If the radiologist finds a suspicious lesion that is otherwise not felt by physical examination, a biopsy needle will be inserted into the lesion site of the anesthetized breast.

After the needle is placed in the breast, another x-ray image will be taken, to determine how close the tip of the needle is to the lesion. Several adjustments of the needle and several x-ray photographs may be required to position the needle at the lesion site. Once the biopsy needle is positioned near the lesion site, a hooked guide wire will be pushed through the biopsy needle and hooked onto the lesion. The guide wire provides the surgeon with a traceable path to the lesion. The surgeon will then remove either a sample of the lesion (i.e. by aspiration biopsy), or the entire lesion by surgical biopsy procedure as well as the guide wire, and the tissue removed will be examined by the pathologist. This process is time consuming, painful, physically scaring, and expensive. The patient will then wait a few agonizing days to learn of the test results. Again, since by x-ray mammography the radiologist cannot readily distinguish between malignant and non-malignant lesions, when suspicious lesions are located, biopsies are required. Statistically 80% of all lesions removed are non-malignant. Present x-ray mammography technique results in many unnecessary biopsies.

Several approaches have been explored to better locate the position of the lesion in a patient's breast by x-ray mammography. U.S. Pat. No. 5,209,232 to Levene uses computerized device to accurately detect the position of lesions in the breast, and to position the biopsy needle. U.S. Pat. No. 5,289,520 to Pellegrino et al. and U.S. Pat. No. 5,078,192 to Siczek et al. provide automated breast lesion locator imaging and biopsy systems.

U.S. Pat. No. 5,056,523 to Hotchikiss, Jr. et al. discloses a device and method for precisely positioning the tip of a probe into a breast lesion. Radiopaque markers are used to identify the position of the lesion relative to a fenestrate compression grid. To determine the depth of the lesion in the breast, a certain amount of trial and error is required. A similar system is provided by the method and apparatus of U.S. Pat. No. 4,875,478 to Chen. The Chen apparatus used a radiolucent compression support plate with calibration marks, with a movable biopsy needle support guide, so that the biopsy needle can be positioned with its tip in the lesion. Notwithstanding the improvements provided by these x-ray mammography devices, major problems remain in that many unnecessary biopsies will still be to be performed.

Another new, experimental method utilizes contrast material-enhanced magnetic resonance (MR) mammography, and is disclosed in "MR Mammographic Localization, Work in Progress", by K. Hussman et al. Radiology, Vol. 189, No. 3, pp. 915–917. By this method, after magnetic resonance enhancing agents are injected into the patient's bloodstream, her breast being examined is placed in an open box with two fenestrated perpendicular side walls. The position of the lesion in the X, Y and Z coordinates is noted, and the precise position of the biopsy needle will then be sought to be located. Since the magnetic resonance apparatus is quite narrow to enter, the needle must be inserted after the patient's breast is imaged. To avoid the breast shifting in the box, the breast is best temporary adhered to the box with medical grade adhesive.

Recently, the use of Technetium-99m Sestamibi (sold under the name Cardiolite®, by the DuPont Merck Pharmaceutical Co., Billerica, Mass.) has been explored to accurately detect the presence of carcinoma of the breast. See "Review of Imaging Techniques for the Diagnosis of Breast Cancer, a New Role of Prone Scintimammography using Technetium-99m Sestamibi", by I. Khalkhali, I. Mena, and L. Diggles, European Journal of Nuclear Medicine, Vol. 21, No. 4, April 1994, pp. 357–362, and "Prone Scintimammography in Patients with Suspicion of Carcinoma of the Breast", by I. Khalkhali, I. Mena, E. Jouanne, L. Diggles, R.

Venegas, J. Block, K. Alle, and S. Klein, Journal of American College of Surgeons, May 1994, Vol. 178, pp.491–97.

Scintimammography, or more generally "nuclear medicine mammography," are methods to detect the presence of malignant lesions by radioactive substances which selectively accumulate in the malignant lesions, or carcinomas.

By utilizing the method of nuclear medicine mammography with Technetium-99m Sestamibi, the inventors have reported a negative predictive value for the presence of carcinoma of 97.5%, a sensitivity of 96%, and a specificity of 85%. More importantly, by the method of nuclear medicine mammography using Technetium-99m Sestamibi, malignant lesions as small as 1 cm can be diagnosed. In this methodology, a scintillation camera is used to detect the radiation given off from the Technetium-99m Sestamibi. In addition to scintillation cameras, newer semiconductor radioactive detectors, such as offered by the Digirad company of San Diego, Calif. can be used, which does not rely on scintillation, but detects the radiation given off. Hereinafter, the term "scintimammography" or "nuclear medicine" shall refer not only to the method which uses a scintillation camera but also includes the method using newer semiconductor detectors.

However, there has not been as of yet a method and apparatus for accurately localizing carcinomas of the breast by real-time scintimammography or other nuclear medicine techniques. There accordingly remains a need for a scintigraphy or nuclear medicine guided stereotaxic localization apparatus and method for carcinomas of the breast.

SUMMARY OF THE INVENTION

A first objective of the invention is to provide a nuclear medicine guided system for stereotaxic localization of breast carcinomas, adapted for use in conjunction with a nuclear medicine detection device, of a patient who has been injected with a radioactive substance which preferentially accumulates in carcinoma lesion sites, said system comprising:

a table means, with a top and bottom surface, upon which the patient lies in a prone position, said table means having at least one opening through which the patient's breast being examined will pendulously protrude therethrough;

a pair of fenestrated paddles positioned under the bottom surface of the table means in the vicinity of said at least one opening, said pair of fenestrated paddles being moveable relative to each other to compress the patient's breast therebetween; and a guide means positioned under the table means in the vicinity of the opening, said guide means having a plurality of moveable sighting guides, each moveable along one of three orthogonal axes, each sighting guide having a radioactive sighting line located thereon, wherein said moveable sighting guides will be moved to line up with the lesion site in the breast, as detected by the nuclear medicine detector device, to localize the lesion in three dimensions and in real-time in the breast.

Another objective of the invention is to provide a nuclear medicine guided system for stereotaxic localization of breast carcinomas, adapted for use in conjunction with a nuclear medicine detection device, of a patient who has been injected with a radioactive substance which preferentially accumulates in carcinoma lesion sites, said system comprising:

a table means, with a top and bottom surface, upon which the patient lies in a prone position, and at least one opening formed through said table means through which the patient's breast being examined will pendulously protrude therethrough;

a pair of fenestrated paddles formed of non-attenuating material and positioned under the bottom surface of the table means in the vicinity of the at least one opening, said pair of fenestrated paddles being moveable relative to each other to compress the patient's breast therebetween; and a guide means positioned under the table means in the vicinity of the opening, said guide means having a plurality of moveable sighting guides, each moveable along one of three orthogonal axes, each sighting guide having a radioactive sighting line located thereon;

wherein in the use of the system, the patient's breast will be compressed by the fenestrated paddles, and a nuclear medicine detection device will be placed adjacent and generally parallel to a first plane defined by two of said three orthogonal axes along which two sighting guides are moveable, to detect radioactive photons given off by the radioactive substance which has accumulated at the lesion site, and said two sighting guides will be moved so their sighting lines project over the center of the lesion site, thus localizing the lesion site in two-dimensions, and the nuclear medicine detection device will be placed parallel to a second plane, orthogonal to said first plane, and in front of the remaining third sighting guide, and the third sighting guide will be moved along the third orthogonal axis, until its sighting line is in line with the center of the lesion site, whereby the three sighting lines of the three sighting guides will thus localizing the lesion site in real-time and in three-dimensions relative to the fenestrated paddles.

Yet another object of the invention is to provide a nuclear medicine guided system for stereotaxic localization of breast lesions, adapted for use in conjunction with a scintillation detection device, of a patient who has been injected with a radioactive substance which preferentially accumulates in carcinoma lesion sites, said system comprising:

a table means, with a top and bottom surface, upon which the patient lies in a prone position, said table means having at least one opening through which the patient's breast being examined will pendulously protrude therethrough;

a pair of paddles positioned under said bottom surface of said table means in the vicinity of said at least one opening, said pair of paddles being moveable relative to each other to slightly compress and thereby stabilize the patient's breast therebetween; and a guide means positioned under said table means in the vicinity of said opening and said paddles, said guide means having a plurality of moveable sighting guides, each moveable along one of three orthogonal axes, each sighting guide carrying a radioactive sighting line, wherein said moveable sighting guides will be moved to line up their radioactive sighting with the lesion site in the breast, as detected by the nuclear medicine detector device, to localize the lesion site in three dimensions and in real-time in the breast.

A further object of the invention is to provide a nuclear medicine guided system for stereotaxic localization of breast lesions of a patient who has been injected with a radioactive substance which preferentially accumulates in carcinoma lesion sites, adapted for use in conjunction with a nuclear medicine detection device, said system comprising:

a table means, with a top and bottom surface, upon which top surface the patient lies in a prone position, said table means having at least one opening through which the patient's breast being examined will pendulously protrude therethrough;

breast compression and stabilizing means located under said bottom surface of said table in a vicinity of said at least one opening which is adapted to stabilize the patient's breast pendulously protruding through said at least one opening; and a guide means positioned under said table means in the vicinity of said opening and said paddles, said guide means having a plurality of moveable sighting guides, each moveable along one of three orthogonal axes, each sighting guide carrying a radioactive sighting line, wherein said moveable sighting guides are movable so their radioactive sighting will line up with a lesion site in the breast, as detected by the scintillation detector device, to localize the lesion site in three dimensions and in real-time in the breast.

A final aspect of the invention is to provide a method for nuclear medicine localization of breast carcinoma lesion sites of a patient who has been administered a radioactive substance which gives off radiation and which preferentially accumulates in breast lesion sites, said method system comprising the following steps:

(a) providing a table means having a top and bottom surface with at least one opening formed therethrough;

(b) lying a patient in a prone position on the top surface of the table means such that the patient's breast to be examined will pendulously protrude therethrough;

(c) administering a radioactive substance which preferentially accumulates in breast carcinoma lesion sites of the patient;

(d) lightly compressing the patient's breast being examined with a pair of paddles positioned on the bottom surface of the table means in order to generally immobilize the patient's breast being examined;

(e) providing a guide means on the bottom surface of said table means in the vicinity of said opening and said pair of paddles, said guide means having a plurality of moveable sighting guides, each moveable along one of three orthogonal axes, each sighting guide carrying a radioactive sighting line;

(f) providing a nuclear medicine detection device with a detector;

(g) orienting the nuclear medicine detector such that it is placed adjacent the breast being examined and is generally parallel to two of the three orthogonal sighting guides in a first plane such that the two sighting guides are situated between the detector and the breast so, radiation given off by the two sighting guides' sighting lines and the carcinoma are detected by the nuclear medicine detection device;

(h) moving said two moveable sighting guides until their radioactive sighting lines line up with a carcinoma lesion site in the breast, as detected by the nuclear medicine detector device, in two-dimensions and in real time;

(i) orienting the detector such that it is placed generally perpendicular to the first plane, such that the third sighting guide is situated between the detector and the breast so radiation given off by the third sighting guide's sighting line and the carcinoma lesion site are detected by the nuclear medicine detector; and (j) moving said third sighting guide until its radioactive sighting line lines up with the carcinoma lesion site in the breast, as detected by the nuclear medicine detector device, thereby locating the carcinoma lesion site in three dimensions and in real time.

DETAILED DESCRIPTION OF THE PREFERRED EMBODIMENT

Referring to FIGS. 1 and 2–5 there is illustrated a nuclear medicine guided stereotaxic localization apparatus 10 for breast carcinomas. The apparatus 10 has a generally horizontal table portion 12 with an upper surface 14 upon which a patient lies, and a lower, underside surface 16. Openings or cut-outs 18 are formed on opposite side regions 20 of the table portion 12. The openings 18 are separated by an intermediate table portion 22 sufficiently wide such that when the patient lies prone on the table portion 12, the breast not being examined will be supported on the intermediate table portion 22.

Figure 1:
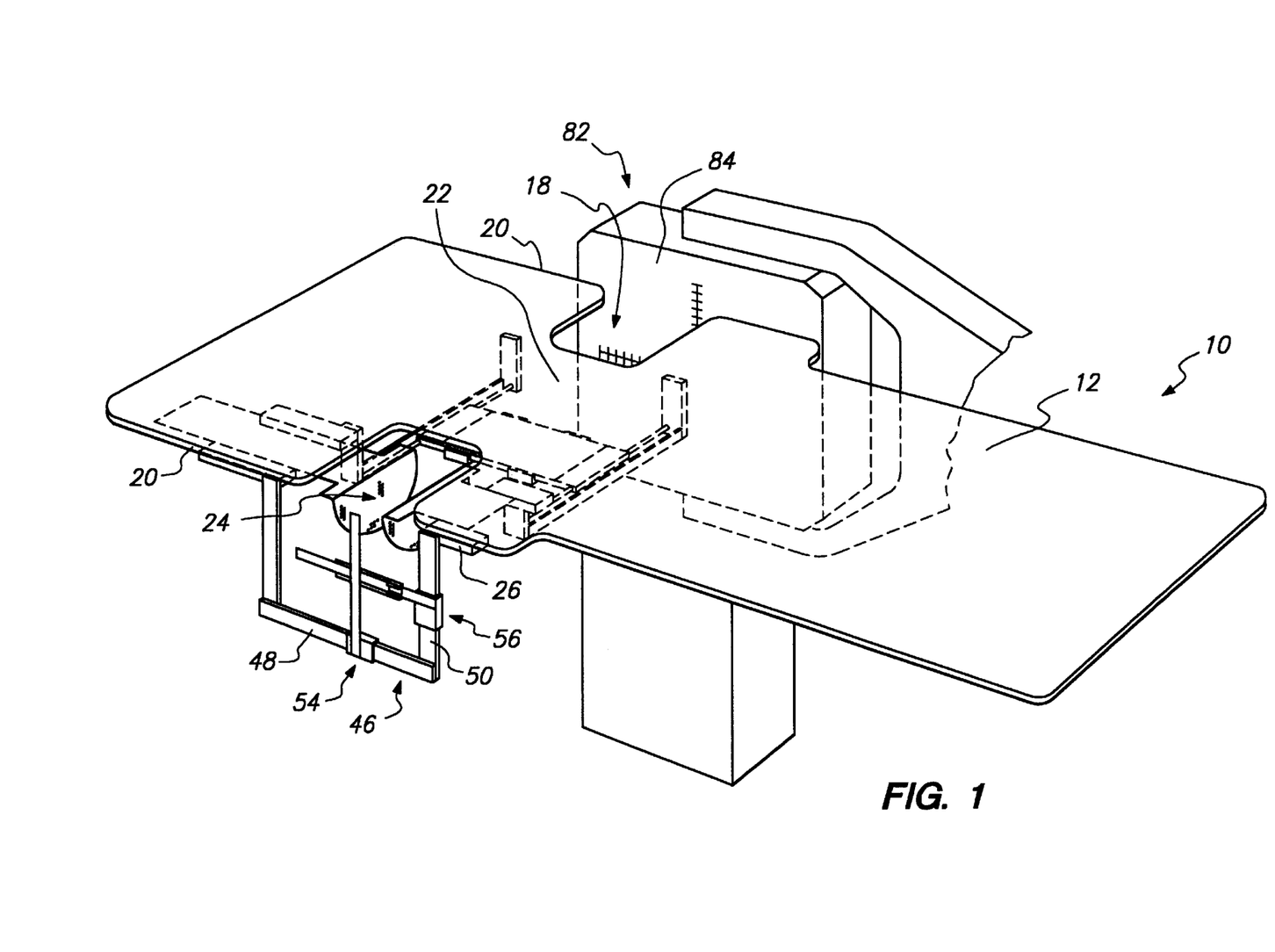
FIG. 1 is a perspective partially exposed view of the apparatus of the invention, and a nuclear medicine detector.

A pair of fenestrated paddles 24 are positioned under the table 12, and slide in slider guides 26 mounted to the underside 16 of the table 12.

Figures 2, 3:
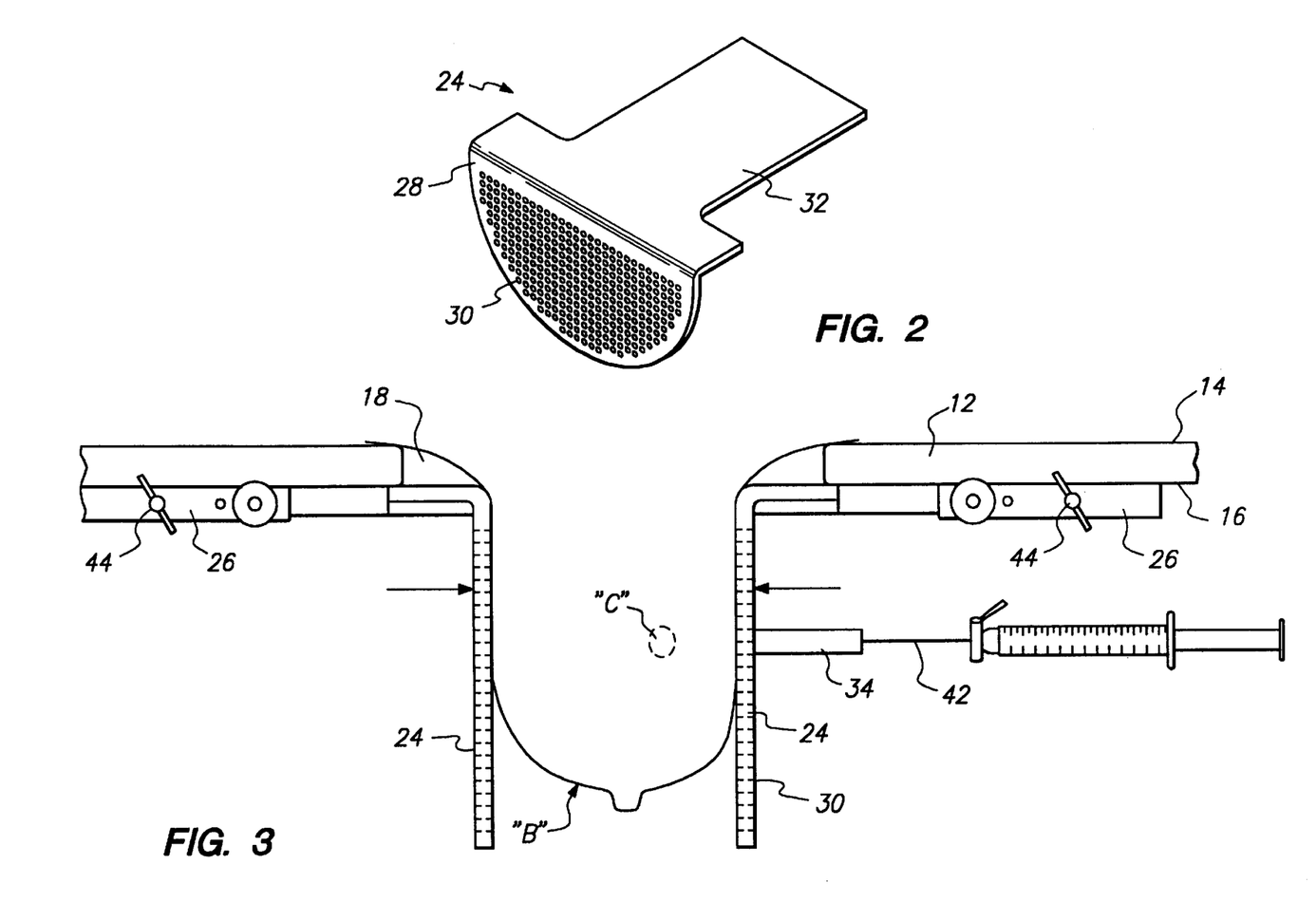
FIG. 2 is a perspective view of a fenestrated paddle of the system.
FIG. 3 is a partial side view of the system showing a patient's breast being compressed between the fenestrated paddles, less the sliding guides, with needle guide and a syringe.

Best referring to FIG. 2, each fenestrated paddle 24 has a planar, breast compression portion 28 with a large number of holes 30 formed therethrough. These holes 30 are formed evenly spaced in the breast compression portion 28 in preferably a uniform grid pattern. Extending generally perpendicular from the planar compression portion 28 is a slider bar portion 32. The holes 30 can be placed as close as one to two millimeters apart, and are sized to receive a optional needle guide 34. The needle guide 34 has an insertion portion which fits into a hole 30, and an elongate body. The needle guide 34 has a coaxial hole (not shown) which is sized to fit a needle 42, and the needle guide thus serves to guide the needle into the breast at right angles to the breast compression portion 28 of the fenestrated paddle 24. The apparatus 10 is designed to accommodate both 23 gauge and 16 gauge needles 42, permitting fine needle aspiration and core biopsies, respectively, to be performed. Other gauge needles can also be utilized. Where core biopsies are taken, the core biopsy guide wire 42 will preferably have a Cobalt-57 tip protected by Teflon® (to prevent any possibility of Cobalt-57 being left in the patient's breast).

The fenestrated paddle 24 is best formed of radioactive non-attenuating material, so as not to absorb the radioactive photons given off from the radioactive material (viz. Technetium-99m Sestamibi or any other radiopharmaceutical). The inventors have found plastics such Plexiglas®, and particularly Lexan® to be good materials for the construction of the compression paddles 24, with Lexan® being a preferred choice because of its great durability. Preferably, in order to avoid cross-contamination between patients, the needles and guide wires and needle guide 34 are designed for single use, and should be disposed of after use. The close spacing of the holes 30 in the compression portion 28 permits the accurate biopsy of extremely small lesions.

Figure 4:
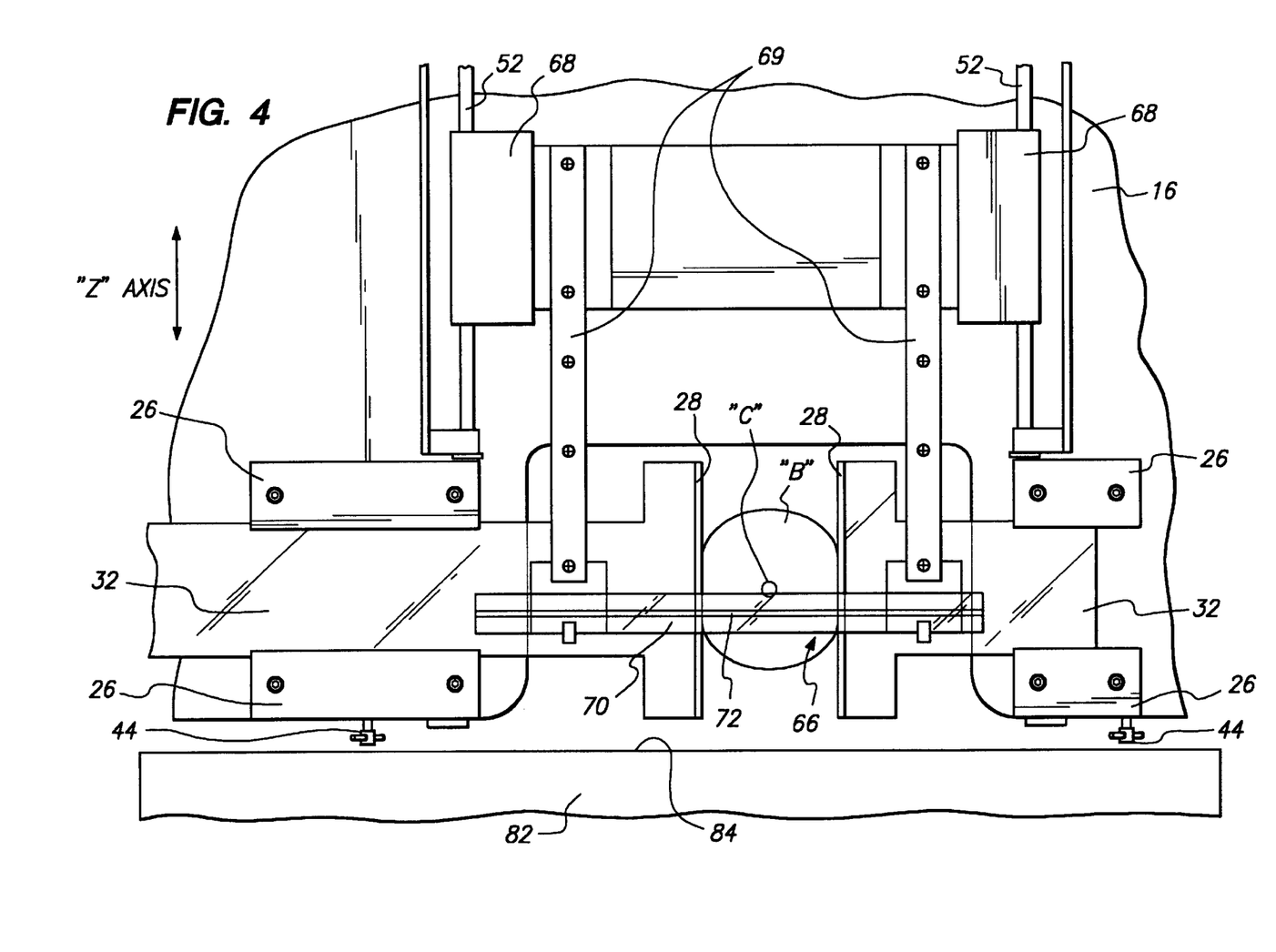
FIG. 4 is a bottom-up view of the system, showing a patient's breast being compressed, one sighting guide, and the nuclear medicine detector.

Referring to FIGS. 3 and 4, the slider bar portions 32 of the compression paddles 24 slide in the slides guide 26. A means is provided to immobilize the two paddles 24 relative to the breast compressed therebetween. This can, for example, comprise a thumbscrew 44 threaded through a bore in the slider guide 26, whose end frictionally engages with the slides bar portion 32, to thereby immobilize it in a desired position. If desired, one fenestrated paddle 24 can be made to be stationary (not shown).

Unlike the methods of x-ray mammography, in nuclear medicine guided localization, the breast need not be compressed to a great degree. Rather, the degree of compression required is that which is enough to flatten the breast against the fenestrated paddles 24, as is best shown in FIGS. 3–5.

Figure 5:
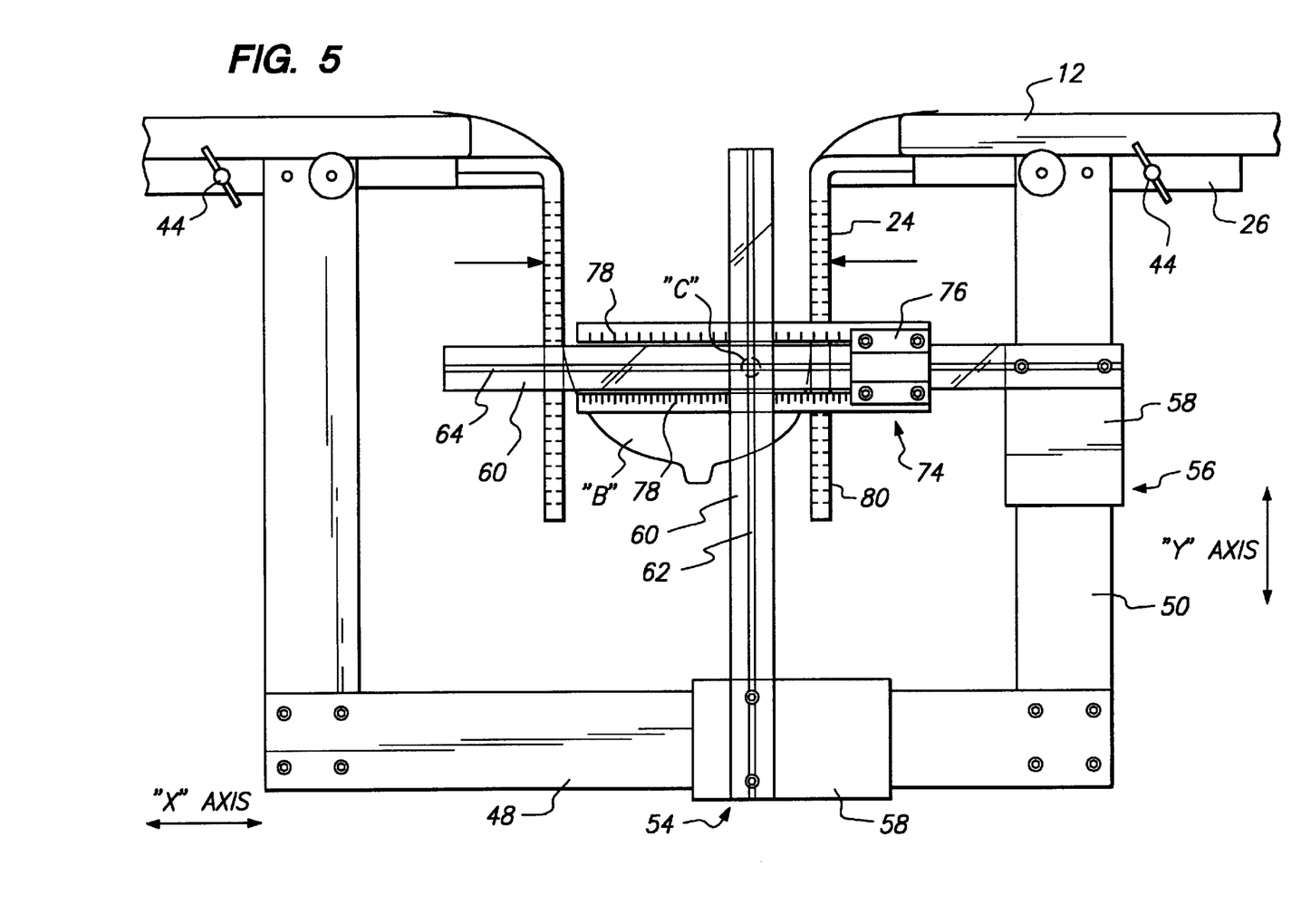
FIG. 5 is a partial side view of the system, showing two sliding guides lined up with a lesion site.

Referring to FIGS. 1, 4, and 5 a positioning guide means or rack means 46 is mounted to the underside 16 of the table portion in the vicinity of the openings 18. The rack means 46 has a horizontal track portion 48 which lies horizontally, along an "X" axis, and a vertical track portion 50, which lies vertically, along a "Y" axis. Referring to FIG. 4, the rack means also has track portions 52 which lies along a "Z" axis. The track portions 48 and 50 provide tracks, upon which moveable sighting guides 54 and 56, respectively, slide.

The sighting guides 54 and 56 have track engagement sliders 58, which slidable engage with the track portions 48 and 50. Materials such as Nylon® and Teflon® plastic work well, as they can be made to smoothly slide on the track portions 48 and 50. Materials such as aluminum alloy can be used to form the track portions 48, 50 and 52. Extending outwardly at a right angles from the track engagement slides are elongate carrier portions 60, formed of non-attenuating material such as Plexiglass®, Lexan®, and other plastic materials. The carrier portions 60 each carry a radioactive sighting line 62 and 64, respectively. The inventors use a Cobalt-57 containing wire. The sighting line 62 of the sighting guide 54 lies along a "Y" axis and the sighting line 64 of sighting guide 56 lies on an "X" axis. The sighting guides 54 and 56 can be moved, until their sighting lies 62 and 64 line up with the "X" and "Y" coordinates of the carcinoma site "C", as will be described in greater detail further below.

Referring to FIG. 4, the rail portions 52 which lie in a plane parallel to the underside 16 of the table portion lie on "Z" axes and carry a moveable sighting guide 66, which spans the two rail portions 52, and is slidable thereon. The horizontal sighting guide 66 has slider guides 68 which actually slide on the rail portion 66, support arms 69 which extend therefrom, and a carrier portion 70. As with the other moveable sighting guides 54 and 56, the carrier portion 70 is formed of a non-attenuating material, such as Lexan® or Plexiglass®. The carrier portion 70 carries a radioactive sighting line 72, which can comprise a capillary tube filled with a radioactive substance, such as Cobalt-57. The horizontal sighting guide 66 will be moved until its sighting line 72 lines up with the center of lesion site "C", along the Z-axis, in a manner which will be discussed in greater detail below. By use of the three moveable sighting guides 54, 56 and 66, the lesion site "C" can be accurately localized in its X, Y and Z coordinates, in real-time.

Referring to FIG. 5, the moveable sighting guide 56 carries a slidable ruler means 74, which has a slider portion 76 which slides on the carrier portion 60 of sighting guide 56, and a ruler portion 78 extending therefrom. A ruler portion 78 lies parallel to the carrier portion 60. The slidable ruler means 74 can be moved on the carrier portion 60 to measure the distance from the outside face 80 of the fenestrated paddle 24 closest to the vertical track portion 50, to the crossing point of the sighting lines 60 and 62, to determine the needle 42 penetration needed to reach the center of the carcinoma site "C".

The operation of the apparatus 10 is now described. A woman patient has had indeterminate mammogram with normal physical breast examination and who desires to have a breast carcinoma screening by the method of nuclear medicine mammography will be injected with a compound such as Technetium-99m Sestamibi. The patient will lie on the table 12 with her breast to be examined pendulously suspended through one of the two openings 18. Referring to FIGS. 3–5, the paddles 24 will be moved so that the patient's breast is compressed at least slightly to immobilize it and so that the breast will be flattened against the fenestrated paddle 24. Thereafter, a nuclear medicine detection device 82, such as an Anger scintillation camera or a newer, digital camera, such as offered by Digirad of San Diego, Calif. will be placed with its detection screen 84 parallel to the plane of the moveable sighting guides 54 and 56. The sighting guides 54 and 56 will be moved so their sighting lines 62 and 64, respectively, line up in the "X" and "Y" positions with the center portion of any lesion site "C" detected. The nuclear medicine detection device 80 will then be moved so that its screen 84 is parallel with the plane of the lower surface of the table portion 12, and parallel to the horizontal sighting guide 66. As shown in FIG. 4, the radioactive sighting line 62 will be aligned with the center of the lesion site "C", thereby determining its position in the "Z" axis. By the use of the three sighting guides 54, 56, and 66, the X, Y, and Z coordinates of the lesion site "C" will be quickly and accurately determined. Once the sighting guides are positioned, the physician will know which hole 30 in the grid of holes in the fenestrated paddle 24 to insert the needle guide 34 and needle 42. The ruler means 74 will give the physician accurate feedback as to how deep to insert the needle 42, to that its tip can be positioned where desired in the lesion site "C". For, enhanced function, needles 42 having a radioactive tip (not shown) can be utilized to confirm the accurate positively of the needle 42 in real-time 42. Again, the radioactive isotope Cobalt-57 functions well, but other radioactive materials can be utilized as long as it has a different spectrum from radioactive material that is injected is the patient's veins. The apparatus 10 can thus be used to accurately localize carcinoma sites in real-time without greatly compressing the patient's breast.

EXAMPLE

The accuracy of the above-referenced apparatus 10 and system in localizing carcinoma sites was tested in vitro as described below.

A semi-square sponge breast phantom was placed between the fenestrated paddles 24, and was compressed in the cranial and caudal directions by the fenestrated paddles 24. To create a radioactive background similar to the radioactivity in normal breast tissue, a thin sponge was moistened with a dilute solution of Technetium-99m, sealed in a plastic bag, and attached to the surface of a nuclear medicine scintillation detector. A large synthetic sponge with no radioactivity added was used to represent the breast. A small piece was carved out of the interior of the sponge at a depth of 2~6.7 cm, labeled with a small amount of radioactivity, and reinserted in the sponge to represent a nonpalapable tumor. The "tumors" ranged from 3 mm to 15 mm in size. Thallium-201 was used to label the tumors because the energy of its emissions differs enough from those of technetium to allow separate images of each energy, as well as a combined image of the two. In actual practice, for patient use, a high tumor-affinity radiopharmaceutical such as Technetium-99m Sestamibi alone will be used. The sponge breast phantom containing the lesion was placed between two fenestrated paddles 24 and held in place with mild compression by the paddles 24. The nuclear medicine detector was positioned near the phantom and real-time images were acquired in two orthogonal planes. The sliding guides 54, 56 and 66 were moved so that their radioactive sighting lines 62, 64 and 72, respectively, projected onto the nuclear medicine detector screen 84, intersecting with the detected position of the "lesion".

Moveable sighting guides 54, 56 and 66 utilizing Technetium-99m Sestamibi in lieu of (Cobalt-57 in its capillary tubes were used to locate the X, Y, and Z coordinates of the lesion site.

A needle guide 34 was placed in the hole corresponding to the X and Y coordinates of the "tumor" to allow the needle 42 to be inserted perpendicular to the breast compression portion 28. When the needle tip was advanced to the correct depth of the "tumor", Technetium-99m was injected through the needle 42 into the sponge breast phantom. Pre and post localization attempt regions of interest (ROI) were defined, and also, the residual activity in the phantom was measured.

Figure 6:
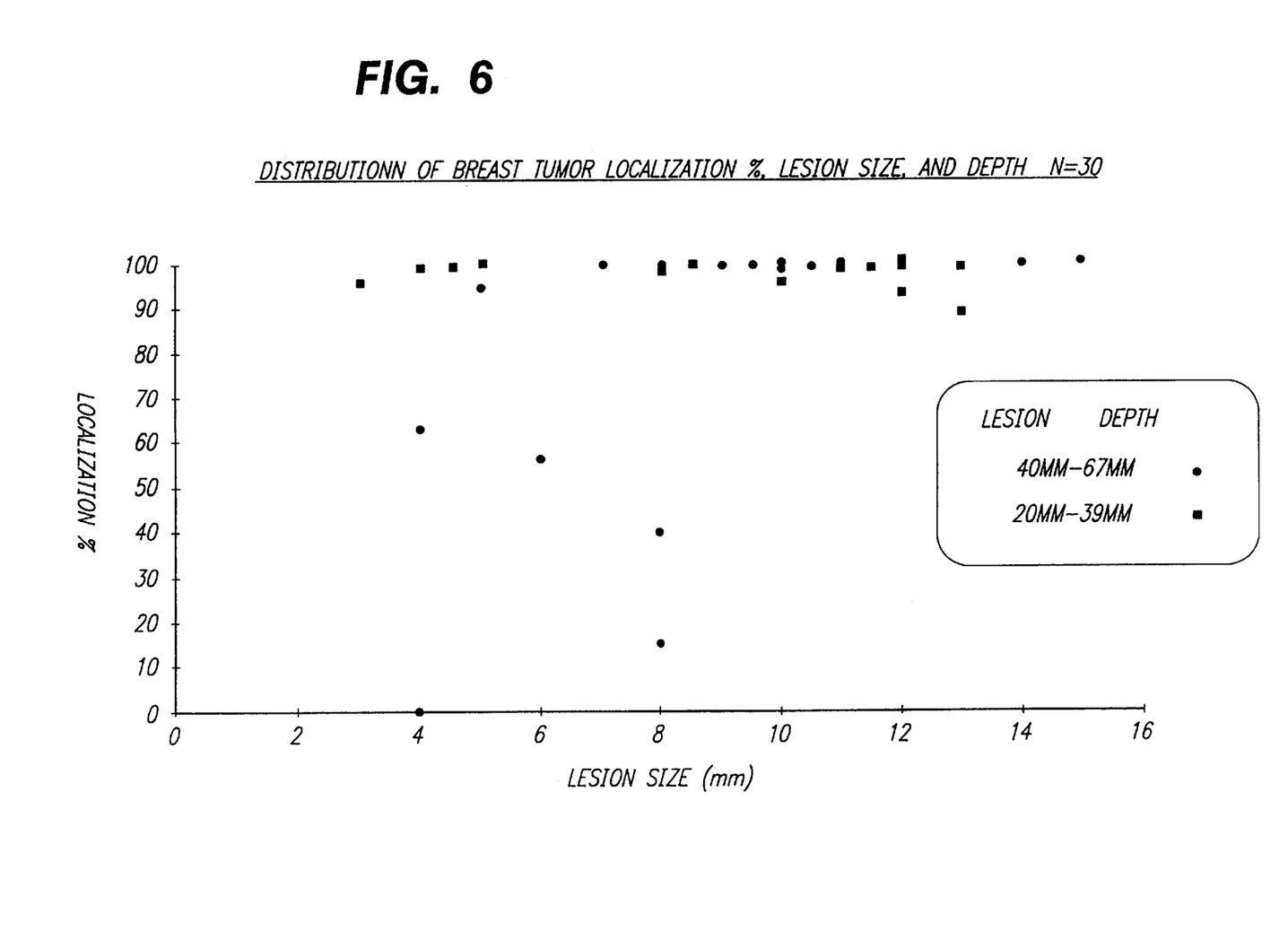
FIG. 6 is distribution of breast tumors localizations in a phantom breast.

To determine the success of the injection, the "tumor" was carefully removed from the phantom, and an image of the empty phantom was acquired. If the radioactive solution was injected within the tumor, the phantom would not contain radioactivity. If the lesion was "missed," the radioactivity remained in the phantom and appeared on the image. Partial "misses" contain an intermediate amount of the radioactivity in the injection. The amount of total radioactivity injected and the amounts remaining in the phantom were quantified to give the results represented on FIG. 6.

The results of 30 consecutive localization attempts include: 25 exact localizations with more than 80% of tracer injected inside the "lesion", 2 near misses with 63% to 56% , and 3 missed locations with 40% , 15% , and 0% of tracer injected inside the lesion. The missed localizations were all in lesions at least 4 cm deep, and all had partially superimposed ROIs which indicates the needle came very close to the lesion. The nuclear medicine guide stereotaxic localization system of breast phantom lesions successfully localized 90% of all lesions. Similar results have been observed in in vivo practice.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation, the scope of the invention being delineated in the following claims:

We claim:

1. A nuclear medicine guided system for stereotaxic localization of breast carcinomas, adapted for use in conjunction with a nuclear medicine detection device, of a patient who has been injected with a radioactive substance which preferentially accumulates in carcinoma lesion sites, said system comprising:

a table means, with a top and bottom surface, upon which the patient lies in a prone position, said table means having at least one opening through which the patient's breast being examined will pendulously protrude therethrough;

a pair of fenestrated paddles positioned under the bottom surface of the table means in the vicinity of said at least one opening, said pair of fenestrated paddles being moveable relative to each other to compress the patient's breast therebetween; and a guide means positioned under the table means in the vicinity of the opening, said guide means having a plurality of moveable sighting guides, each moveable along one of three orthogonal axes, each sighting guide having a radioactive sighting line located thereon, wherein said moveable sighting guides will be moved to line up with the lesion site in the breast, as detected by the nuclear medicine detector device, to localize the lesion in three dimensions and in real-time in the breast.

2. The nuclear medicine guided system for stereotaxic localization of breast lesions of claim 1, wherein said guide means comprises track portions oriented along three orthogonal axes, and wherein said moveable sighting guides comprise track engagement sliders which are moveable on said track portions, said moveable sighting guides having elongate and non-attenuating carrier portion which extend from said track engagement sliders, and wherein said radioactive sighting lines are carried on said carrier portions.

3. The nuclear medicine guided system for stereotaxic localization of breast lesions of claim 2, wherein the radioactive sighting lines comprise capillary tubes filled Cobalt-57.

4. The nuclear medicine guided system for stereotaxic localization of breast lesions of claim 2, wherein the radioactive sighting lines comprise Cobalt-57 containing wires.

5. The nuclear medicine guided system for stereotaxic localization of breast lesions of claim 2, wherein the fenestrated paddles comprise a planar breast compression portion with a plurality of holes arranged therethrough in a spaced apart pattern, and a slider portion which extends perpendicularly from said planar breast compression portion, and wherein said slider portion slides in slider guides positioned on the bottom surface of the table means, wherein said fenestrated paddles are selectably immobilizable therein by use of locking means.

6. The nuclear medicine guided system for stereotaxic localization of breast lesions of claim 5, further comprising an elongate ruler slidable on the carrier portions of one of the moveable sighting guides which is used to determine the distance from the breast carcinoma to the planar breast compression portion, so that an individual using the nuclear medicine guided system of the invention can determine how far to insert a guide needle into a patient's breast to place a tip of the guide needle into the site of the lesion.

7. The nuclear medicine guided system for stereotaxic localization of breast lesions of claim 1, wherein the substance which preferentially accumulates in lesions comprises Technetium-99m Sestamibi.

8. The nuclear medicine guided system for stereotaxic localization of breast lesions of claim 1, wherein the fenestrated paddles comprise a planar breast compression portion with a plurality of holes arranged therethrough in a spaced apart pattern, and a slider portion which extends perpendicularly from said planar breast compression portion, and wherein said slider portion slides in slider guides positioned on the bottom surface of the table means, wherein said fenestrated paddles are selectably immobilizable by use of locking means.

9. The nuclear medicine guided system for stereotaxic localization of breast lesions of claim 8, wherein the fenestrated paddles are formed of plastic material.

10. The nuclear medicine guided system for stereotaxic localization of breast lesions of claim 8, further comprising a biopsy needle guide which is fittable into any hole formed in the fenestrated paddles, and which is adapted for use in ensuring that a biopsy needle which is inserted through the biopsy needle guide will penetrate the breast at generally right angles to the breast compression planar portion.

11. The nuclear medicine guided system for stereotaxic localization of breast carcinomas of claim 8, wherein the locking means comprises a thumbscrew screwable in said slider guides to selectable immobilize said slider portion located in said slider guides and its breast compression portion.

12. The nuclear medicine guided system for stereotaxic localization of breast lesions of claim 1, wherein the table means is generally horizontal, and has an elongate shape, wherein the at least one opening comprises two openings formed on opposite side regions of the table means.

13. A nuclear medicine guided system for stereotaxic localization of breast carcinomas, adapted for use in conjunction with a scintillation detection device, of a patient who has been injected with a radioactive substance which preferentially accumulates in carcinoma lesion sites, said system comprising:

a table means, with a top and bottom surface, upon which the patient lies in a prone position, and at least one opening formed through said table means through which the patient's breast being examined will pendulously protrude therethrough;

a pair of fenestrated paddles formed of non-attenuating material and positioned under the bottom surface of the table means in the vicinity of the at least one opening, said pair of fenestrated paddles being moveable relative to each other to compress the patient's breast therebetween; and a guide means positioned under the table means in the vicinity of the opening, said guide means having a plurality of moveable sighting guides, each moveable along one of three orthogonal axes, each sighting guide having a radioactive sighting line located thereon;

wherein in the use of the system, the patient's breast will be compressed by the fenestrated paddles, and a nuclear medicine detection device will be placed adjacent and generally parallel to a first plane defined by two of said three orthogonal axes along which two sighting guides are moveable, to detect radioactive photons given off by the radioactive substance which has accumulated at the lesion site, and said two sighting guides will be moved so their sighting lines project over the center of the carcinoma, thus localizing the carcinoma in two-dimensions, and the nuclear medicine detection device will be placed parallel to a second plane, orthogonal to said first plane, and in front of the remaining third sighting guide, and the third sighting guide will be moved along the third orthogonal axis, until its sighting line is in line with the center of the lesion site, whereby the three sighting lines of the three sighting guides will thus localize the carcinoma in-real-time and in three-dimensions relative to the fenestrated paddles.

14. A nuclear medicine guided system for stereotaxic localization of breast lesions, adapted for use in conjunction with a scintillation detection device, of a patient who has been injected with a radioactive substance which preferentially accumulates in carcinoma lesion sites, said system comprising:

a table means, with a top and bottom surface, upon which the patient lies in a prone position, said table means having at least one opening through which the patient's breast being examined will pendulously protrude therethrough;

a pair of paddles positioned under said bottom surface of said table means in the vicinity of said at least one opening, said pair of paddles being moveable relative to each other to slightly compress and thereby stabilize the patient's breast therebetween; and a guide means positioned under said table means in the vicinity of said opening and said paddles, said guide means having a plurality of moveable sighting guides, each moveable along one of three orthogonal axes, each sighting guide carrying a radioactive sighting line, wherein said moveable sighting guides will be moved to line up their radioactive sighting with the lesion site in the breast, as detected by the nuclear medicine detector device, to localize the lesion in three dimensions and in real-time in the breast.

15. The nuclear medicine guided system for stereotaxic localization of breast lesions of claim 14, wherein the fenestrated paddles comprise a planar breast compression portion with a plurality of holes arranged therethrough in a spaced apart pattern, and a slider portion which extends perpendicularly from said planar breast compression portion, and wherein said slider portion slides in slider guides positioned on the bottom surface of the table means, wherein said fenestrated paddles are selectably immobilizable therein by use of locking means.

16. The nuclear medicine guided system for stereotaxic localization of breast lesions of claim 15, wherein said guide means comprise track portions oriented along three orthogonal axes, and wherein said moveable sighting guides comprise track engagement sliders which are moveable on said track portions, said moveable sighting guides having elongate and non-attenuating carrier portions which extend from said track engagement sliders, and wherein said radioactive sighting lines are carried on said carrier portions.

17. The nuclear medicine guided system for stereotaxic localization of breast lesions of claim 15, further comprising an elongate ruler slidable on the carrier portions of one of the moveable sighting guides, and which is used to determine the distance from the breast lesion site to the planar breast compression portion, so that an individual using the nuclear medicine guided system of the invention can determine how far to insert a guide needle into a patient's breast to place a tip of the guide needle into a site of a carcinoma.

18. The nuclear medicine guided system for stereotaxic localization of breast lesions of claim 14, wherein the radioactive sighting lines comprise Cobalt-57 containing wires.

19. The nuclear medicine guided system for stereotaxic localization of breast lesions of claim 14, wherein said pair of paddles are formed of a radioactive non-attenuating plastic material.

20. The nuclear medicine guided system for stereotaxic localization of breast lesions of claim 14, wherein said table means is generally horizontal and has opposite side regions, and said at least one opening comprises two openings formed on the opposite side regions of the table means.

21. A nuclear medicine guided system for stereotaxic localization of breast lesions of a patient who has been injected with a radioactive substance which preferentially accumulates in carcinoma lesion site, adapted for use in conjunction with a nuclear medicine detection device, said system comprising:

a table means, with a top and bottom surface, upon which top surface the patient lies in a prone position, said table means having at least one opening through which the patient's breast being examined will pendulously protrude therethrough;

breast compression and stabilizing means located under said bottom surface of said table in a vicinity of said at least one opening which is adapted to stabilize the patient's breast pendulously protruding through said at least one opening; and a guide means positioned under said table means in the vicinity of said opening and said paddles, said guide means having a plurality of moveable sighting guides, each moveable along one of three orthogonal axes, each sighting guide carrying a radioactive sighting line, wherein said moveable sighting guides are movable so their radioactive sighting will line up with a carcinoma lesion site in the breast, as detected by the scintillation detector device, to localize the carcinoma lesion site in three dimensions and in real-time in the breast.

22. A method for nuclear medicine localization of breast carcinoma lesion site of a patient who has been administered a radioactive substance which give off radiation and which preferentially accumulates in breast lesion site, said method system comprising the following steps:

(a) providing a table means having a top and bottom surface with at least one opening formed therethrough;

(b) lying a patient in a prone position on the top surface of the table means such that the patient's breast to be examined will pendulously protrude therethrough;

(c) administering a radioactive substance which preferentially accumulates in breast carcinoma lesion sites of the patient;

(d) lightly compressing the patient's breast being examined with a pair of paddles positioned on the bottom surface of the table means in order to generally immobilize the patient's breast being examined;

(e) providing a guide means on the bottom surface of said table means in the vicinity of said opening and said pair of paddles, said guide means having a plurality of moveable sighting guides, each moveable along one of three orthogonal axes, each sighting guide carrying a radioactive sighting line;

(f) providing a nuclear medicine detection device with a detector;

(g) orienting the nuclear medicine detector such that it is placed adjacent the breast being examined and is generally parallel to two of the three orthogonal sighting guides in a first plane such that the two sighting guides are situated between the detector and the breast so, radiation given off by the two sighting guides' sighting lines and the carcinoma are detected by the nuclear medicine detection device;

(h) moving said two moveable sighting guides until their radioactive sighting lines line up with a carcinoma lesion site in the breast, as detected by the nuclear medicine detector device, in two-dimensions and in real time;

(i) orienting the detector such that it is placed generally perpendicular to the first plane, such that the third sighting guide is situated between the detector and the breast so radiation given off by the third sighting guide's sighting line and the carcinoma lesion sites are detected by the nuclear medicine detector; and (j) moving said third sighting guide until its radioactive sighting line lines up with the carcinoma lesion site in the breast, as detected by the nuclear medicine detector device, thereby locating the carcinoma lesion site in three dimensions and in real time.

\* \* \* \* \*